United States Patent [19]

Diamond

[11] 4,166,827

[45] Sep. 4, 1979

[54] BIS-CARBAMYLGUANIDINOAZAALKANE ANTIMICROBIAL COMPOUNDS

[75] Inventor: Julius Diamond, Mountain Lakes, N.J.

[73] Assignee: Cooper Laboratories, Inc., Parsippany, N.J.

[21] Appl. No.: 918,090

[22] Filed: Jun. 22, 1978

Related U.S. Application Data

[63] Continuation-in-part of Ser. No. 735,319, Oct. 26, 1976, Pat. No. 4,110,328, which is a continuation-in-part of Ser. No. 627,139, Oct. 30, 1975, abandoned.

[51] Int. Cl.² .................. C07C 127/15; C07C 127/19; C07D 295/12; A61K 31/17
[52] U.S. Cl. .................. 260/553 R; 260/239 BC; 260/404.5; 260/465 D; 260/543 F; 260/552 R; 260/553 A; 260/501.14; 424/250; 424/322; 544/357; 544/358; 544/380; 560/9; 560/34
[58] Field of Search .................. 260/239 BC, 268 BF, 260/268 B, 268 TR, 553 R, 553 A, 552 R, 404.5, 465 D, 543 F; 560/34, 9; 544/357, 358, 380

[56] References Cited

U.S. PATENT DOCUMENTS

| | | | |
|---|---|---|---|
| 2,139,621 | 12/1938 | Lecher et al. | 260/553 R X |
| 2,684,924 | 7/1954 | Rose et al. | 424/330 |
| 3,101,336 | 8/1963 | James et al. | 260/268 |
| 3,152,181 | 10/1964 | Shapiro et al. | 260/501.14 X |
| 3,183,230 | 5/1965 | Shapiro et al. | 260/501.14 X |
| 4,022,834 | 5/1977 | Gundersen | 260/564 B |
| 4,022,962 | 5/1977 | Diamond | 260/553 A X |
| 4,038,303 | 7/1977 | Bauman | 260/553 A X |
| 4,110,328 | 8/1978 | Diamond | 260/553 R X |
| 4,115,488 | 9/1978 | Diamond | 260/553 A |

*Primary Examiner*—Thomas Waltz
*Attorney, Agent, or Firm*—John J. Kolano; Thomas R. Boland

[57] ABSTRACT

Antimicrobial compounds are disclosed having the formula:

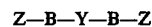

Z—B—Y—B—Z wherein B is carbamylguanidino or thiocarbamylguanidino; Y is an alkylene group which contains one to three nitrogen atoms or which contains two nitrogens as part of a cyclic structure; and Z can represent a number of groups such as alkyl, cycloalkyl, aryl and aralkyl.

15 Claims, No Drawings

BIS-CARBAMYLGUANIDINOAZAALKANE ANTIMICROBIAL COMPOUNDS

REFERENCE TO RELATED APPLICATION

The present application is a continuation-in-part of application Ser. No. 735,319, filed Oct. 26, 1976, now U.S. Pat. No. 4,110,328, which is a continuation-in-part of application Ser. No. 627,139, filed Oct. 30, 1975, and now abandoned.

BACKGROUND OF THE INVENTION

This invention relates to novel compounds which are useful as topical antimicrobial agents and more particularly to antimicrobial compounds which are effective against the microorganisms that produce dental plaque, which have a prolonged intraoral residence time and antimicrobial activity, which have an acceptable taste, and which do not stain the teeth or gums.

Dental plaque is a soft, tenacious bacterial deposit which forms on the surface of the teeth. It is produced by the action of certain bacteria viz., *S. mutans, A. viscosus,* and *A. naeslundi,* on carbohydrate substances in the mouth. Of the numerous antimicrobial agents that have been investigated for their ability to inhibit plaque formation, only 1,6-bis-(p-chlorophenylbiguanidino)-hexane (chlorhexidine) and 1,6-bis-(2-ethylhexyl-biguanidino)hexane (alexidine) are reported to be clinically effective antiplaque agents. However, because these agents are extremely strong organic bases, and consequently are almost entirely cationic at the prevailing pH of the mouth, they suffer from the following disadvantages: (1) they are extremely bitter-tasting substances with a prolonged bitter after-taste lasting up to several hours, (2) they alter taste perception of foodstuffs for several hours, (3) with prolonged use they produce stains of various colors on the teeth, tongue, gums, oral mucosa, (4) they produce local irritation of the oral mucosa and tongue.

A class of carbamylguanidine topical antimicrobial compounds which avoids some of the deficiencies of the prior art compounds is disclosed in U.S. patent application Ser. No. 546,549, now U.S. Pat. No. 4,022,962. This application discloses further carbamylguanidine antimicrobial compounds having improved properties with respect to both the bis-biguanide antimicrobials and the compounds of U.S. Ser. No. 546,549, now U.S. Pat. No. 4,022,962.

SUMMARY OF THE INVENTION

It is accordingly the objective of this invention to provide novel compounds which are useful as topical, nonsystemic antimicrobial agents. A further objective is to provide novel antimicrobial compounds which can reversibly adsorb to teeth and oral mucosa and which are prolonged-acting inhibitors of plaque producing bacteria, which are relatively safe to mammals by oral administration, which have an acceptable taste and do not alter taste perception, and which do not stain teeth, gums, tongue or oral mucosa.

It has now been found that the objectives of this invention can be attained by providing antimicrobial compounds related to the bis-biguanides, but in which the strongly basic biguanide functions have been replaced by the weaker basic functions carbamylguanidino, or thiocarbamylguanidino. The objectives of this invention have been attained by using novel compounds of the formula:

$$Z-B-Y-B-Z$$

wherein B is carbamylguanidino or thiocarbamyl-guanidino, Y is a nitrogen-containing alkylene group having the structural formula

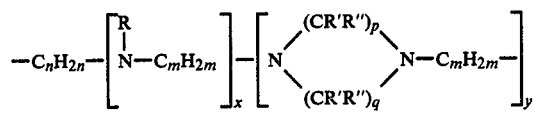

wherein:
$n = 2-4$
$m = 2-4$
$p = 2,3$
$q = 2-4$
$x = 0-3$
$y = 0-2$ and $x=0$ when $y \neq 0$ and $y=0$ when $x \neq 0$, and R is hydrogen or a $C_1$-$C_8$ hydrocarbon radical selected from the group consisting of alkyl, alkenyl, alkynyl, cycloalkyl and aralkyl radicals, and R' and R" are each hydrogen or $C_1$-$C_4$ alkyl and may be the same or different, and Z is selected from the group consisting of $C_1$-$C_{12}$ alkyl; di($C_1$-$C_{10}$)alkylamino-$C_{10}$-$C_2$ alkyl having a total carbon content of $C_4$-$C_{12}$; $C_3$-$C_{12}$ alkenyl; $C_3$-$C_{12}$ alkynyl; $C_3$-$C_{12}$ cycloalkyl; $C_4$-$C_{12}$ cycloalkylalkyl; $C_6$-$C_{12}$ cycloalkenyl; $C_7$-$C_{14}$ cycloalkenylalkyl; $C_7$-$C_{12}$ polycycloalkyl; $C_8$-$C_{14}$ polycycloalkylalkyl; $C_7$-$C_{12}$ polycycloalkenyl; $C_8$-$C_{14}$ polycycloalkenylalkyl; $C_1$-$C_{10}$ alkoxy-$C_{10}$-$C_2$ alkyl having a total carbon content of $C_3$-$C_{14}$; $C_1$-$C_{10}$ alkylthio-$C_{10}$-$C_2$ alkyl having a total carbon content of $C_3$-$C_{14}$; phenoxy $C_2$-$C_6$ alkyl; phenylthio $C_2$-$C_6$ alkyl; $C_6$-$C_{14}$ aryl; $C_7$-$C_{14}$ aralkyl and arylcycloalkyl; $C_9$-$C_{12}$ benzocycloalkyl, and $C_6$-$C_{14}$ aryl and aralkyl substituted with one or more radicals selected from the group consisting of loweralkyl, trifluoromethyl, loweralkoxy, trifluoromethoxy, phenoxy, loweralkylthio, halo, nitro, cyano, $C_2$-$C_6$ alkanoyl, benzoyl, alkoxycarbonyl, diloweralkylamino, loweralkylsulfonyl, fluorosulfonyl and alkylsulfinyl; and pharmacologically acceptable addition salts of these compounds with acids represented by rHA in which r=¼, ⅓, ½, ⅔, ¾, 1, 5/4, 4/3, 3/2, 5/3, 2, 5/2, 3, 4, 5 and HA is an inorganic or organic acid. Lower alkyl denotes an alkyl group containing 1-6 carbon atoms.

The term "carbamylguanidino" includes both unsubstituted and loweralkyl-substituted groups having the formula:

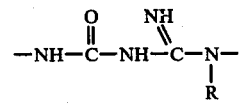

wherein R may be hydrogen or $C_1$-$C_8$ alkyl.

The central group Y may be connected to the substituted guanidino group B either through the guanidino portion of the group or through the carbamyl or thiocarbamyl portion. Thus the invention includes compounds of the following structures:

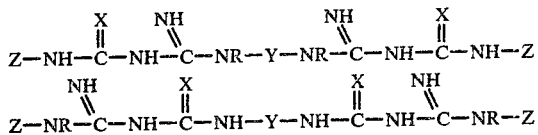

wherein X represents O or S and the other symbols are as defined above.

The carbamylguanidino compounds of this invention, while retaining the desirable antimicrobial activity of the bis-biguanide compounds, provide useful improvements over the latter substances. The carbamylguanidino compounds of this invention reversibly bind to teeth and oral mucosa to provide a prolonged intra-oral residence time and antimicrobial activity, have an acceptable taste, and are relatively safe to mammals by oral administration.

A particular deficiency of the bis-biguanide topical antimicrobials such as chlorhexidine when used to prevent dental plaque formation is staining of the teeth, tongue, and gums which accompanies their prolonged use as mouth rinses. A staining mechanism proposed by Nordbö (Nordbö, Scand. J. Dental Res., 79, 356 (1971) postulates a reaction of chlorhexidine with aldehydes and ketones which are found in the mouth as components of microbial metabolism, and are also present in the glycoprotein constituent of the dental pellicle. The reaction products are colored and could adhere to the teeth, gums and tongue, forming an unsightly deposit. The ability of chlorhexidine to form such colored products by reaction with aldehydes and ketones is believed to reside in the biguanide portion of the molecule and particularly in the presence of the two imino groups of the biguanide radical. The carbamylguanidine compounds of this invention do not have the two imino groups found in the biguanide radical. Hence, the compounds of this invention are unable to undergo the color-forming reaction of biguanides such as chlorhexidine with aldehydes and ketones.

The bis-carbamylguanidinoazaalkanes of this invention, by reason of the basic nitrogen atoms on the Y group, can form acid addition salts having greater water-solubility and longer intraoral residence time and antimicrobial activity than the bis-carbamylguanidinoalkanes of U.S. Ser. No. 546,549, now U.S. Pat. No. 4,022,962. The additional water-solubility of these salts is a useful improvement over the art represented by the compounds of U.S. Ser. No. 546,549, now U.S. Pat. No. 4,022,962.

DESCRIPTION OF THE PREFERRED EMBODIMENTS

In the Y portion of the molecule of the compounds of this invention, the chain of atoms may be straight, or branched, or may contain a cyclic structure.

Suitable Y groups include 3-aza-1,5-pentanediyl, 3-methyl-3-aza-1,5-pentanediyl, 3-ethyl-3-aza-1,5-pentanediyl, 3-n-propyl-3-aza-1,5-pentanediyl, 3-isopropyl-3-aza-1,5-pentanediyl, 3-n-butyl-3-aza-1,5-pentanediyl, 3-(1-methylpropyl)-3-aza-1,5-pentanediyl, 3-isobutyl-3-aza-1,5-pentanediyl, 3-t-butyl-3-aza-1,5-pentanediyl, 3-n-pentyl-3-aza-1,5-pentanediyl, 3-(1-methylbutyl)-3-aza-1,5-pentanediyl, 3-(2-methylbutyl)-3-aza-1,5-pentanediyl, 3-(3-methylbutyl)-3-aza-1,5-pentanediyl, 3-(1-ethylpropyl)-3-aza-1,5-pentanediyl, 3-n-hexyl-3-aza-1,5-pentanediyl, 3-(1-methylpentyl)-3-aza-1,5-pentanediyl, 3-allyl-3-aza-1,5-pentanediyl, 3-propargyl-3-aza-1,5-pentanediyl, 3-cyclopentyl-3-aza-1,5-pentanediyl, 3-cyclohexyl-3-aza-1,5-pentanediyl, 3-benzyl-3-aza-1,5-pentanediyl, 3-aza-1,6-heptanediyl, 4-aza-1,7-heptanediyl, 4-methyl-4-aza-1,7-heptanediyl, 4-ethyl-4-aza-1,7-heptanediyl, 3-aza-1,7-heptanediyl, 2,4-dimethyl-3-aza-1,5-pentanediyl, 2,3,4-trimethyl-3-aza-1,5-pentanediyl, 1,5-dimethyl-3-aza-1,5-pentanediyl, 1,3,5-trimethyl-3-aza-1,5-pentanediyl, 5-aza-1,9-nonanediyl, 5-methyl-5-aza-1,9-nonanediyl, 1,7-dimethyl-4-aza-1,7-heptanediyl, 1,4,7-trimethyl-4-aza-1,7-heptanediyl, 3,6-diaza-1,8-octanediyl, 3,6-dimethyl-3,6-diaza-1,8-octanediyl, 3,6-diethyl-3,6-diaza-1,8-octanediyl, 4,8-diaza-1,11-undecanediyl, 4,8-dimethyl-4,8-diaza-1,11-undecanediyl, 2,5,7-trimethyl-3,6-diaza-1,9-nonanediyl, 5-methyl-3,7-diaza-1,9-nonanediyl, 3,6,9-triaza-1,11-undecanediyl, 3,6,9-trimethyl-3,6,9-triaza-1,11-undecanediyl, 1,4-piperazinediylbis(2,1-ethanediyl), 1,4-(1,4-diazacycloheptanediyl)bis(3,1-propanediyl), 1,4-(1,4-diazacyclooctanediyl)-bis(2,1-ethanediyl), 1,4-piperazinediylbis(3,1-propanediyl), 1,4-piperazinediylbis(2-methyl-2,1-ethanediyl), 1,4-piperazinediylbis(1-methyl-2,1-ethanediyl), 1,4-piperazinediylbis(4,1-butanediyl), cis-2,5-dimethylpiperazinediylbis(3,1-propanediyl), trans-2,5-dimethylpiperazinediylbis(3,1-propanediyl), 1,2-ethanediylbis[4-(piperazinyl(2,1-ethanediyl))] and the like.

Among these groups the preferred groups are 3-loweralkyl-3-aza-1,5-pentanediyl, 3-loweralkyl-3-aza-1,6-hexanediyl, 5-loweralkyl-5-aza-1,7-heptanediyl, 4-loweralkyl-4-aza-1,8-octanediyl, 7-loweralkyl-7-aza-1,9-nonanediyl, 1,4-piperazinediylbis(loweralkanediyl), 1,4-diazacycloheptanediylbis(loweralkanediyl), 1,4-diazacyclooctanediylbis(loweralkanediyl), 1,5-diazacyclooctanediylbis(loweralkanediyl). More preferred groups are 3-methyl-3-aza-1,5-pentanediyl, 4-methyl-4-aza-1,7-heptanediyl, 5-methyl-5-aza-1,9-nonanediyl, 3,6-dimethyl-3,6-diaza-1,8-octanediyl, 4,7-dimethyl-4,7-diaza-1,10-decanediyl, 1,4-piperazinediylbis(2,1-ethanediyl), 1,4-piperazinediylbis(3,1-propanediyl), 1,4-piperazinediylbis(1-methyl-2,1-ethanediyl), 1,4-piperazinediylbis(2-methyl-2,1-ethanediyl), 1,4-piperazinediylbis(2-methyl-3,1-propanediyl), 1,4-(1,4-diazacycloheptanediyl)bis(3,1-propanediyl) and 1,4-piperazinediylbis(4,1-butanediyl).

Preferred for group B are carbamylguanidino groups, and the preferred compounds containing these groups are those in which the guanidino portion of the group is bonded to the central group Y. Thus the preferred compounds are those having the formula:

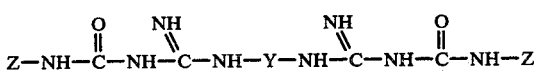

Suitable groups for Z in the novel compounds include: $C_1-C_{12}$ alkyl, e.g., methyl, ethyl, 1-propyl, 1-butyl, 1-pentyl, 1-hexyl, 1-heptyl, 1-octyl, 1-nonyl, 1-decyl, 1-undecyl, 1-dodecyl, 2-propyl, i-butyl, t-butyl, 2-pentyl, i-pentyl, neopentyl, 1-methylpentyl, 2-methylpentyl, 3-methylpentyl, 4-methylpentyl, 2-ethylbutyl, 1-methylhexyl, 2-ethylhexyl, 2-methylheptyl, 1,5-dimethylhexyl, 1,2-dimethylpentyl, 1,3-dimethylpentyl, 1,4-dimethylpentyl, 1,1,3,3-tetramethylbutyl; di($C_1-C_{10}$)alkylamino $C_{10}-C_2$ alkyl e.g., diethylaminoethyl, 2-(N-piperidino)ethyl, 2-(N- morpholino)ethyl; $C_3-C_{12}$ alkenyl, e.g., allyl, 10-undecenyl, 2-ethyl-2-hexenyl, 2,4-dimethyl-2-penten-3-yl, 9-decenyl, 5-hexen-3-yl; $C_3-C_{12}$ alkynyl, e.g., 2-propynyl, 2-butynyl, 2-pentynyl, 2-dodecynyl, 3-butynyl, 4-ethyl-1-hexyn-3-yl; $C_3$–$C_{12}$ cycloalkyl, e.g., cyclopropyl, cyclobutyl, cyclopentyl, 1-methylcyclopentyl, 2-methylcyclopentyl, 3-methylcyclopentyl, cyclohexyl, 1-methylcyclohexyl, 2-methylcyclohexyl, 3-methylcyclohexyl, 4-methylcyclohexyl, 2-isopropyl-5-methylcyclohexyl, 5-isopropyl-2-methylcyclohexyl, cycloheptyl, cyclooctyl, cyclononyl, cyclodecyl, cyclododecyl; $C_4$–$C_{12}$ cycloalkylalkyl, e.g., cyclopropylmethyl, cyclobutylmethyl, cyclopentylmethyl, cyclohexylmethyl, cycloheptylmethyl, 1-cyclohexylethyl, 2-cyclohexylpropyl, cyclooctylmethyl; $C_1$–$C_{10}$ alkoxy-$C_{10}$–$C_2$ alkyl, e.g., 2-ethoxyethyl, 2-butoxyethyl, 2-hexoxyethyl, 3-hexoxypropyl, $C_6$–$C_{12}$ cycloalkenyl, e.g., 2-cyclohexenyl, 3-cyclohexenyl; $C_7$–$C_{14}$ cycloalkenylalkyl, e.g., 2-cyclohexenylmethyl, 3-cyclohexenylmethyl, 2-(3-cyclohexenyl)ethyl; $C_7$–$C_{12}$ polycycloalkyl, e.g., cis-hexahydroidan-5-yl, trans-hexahydroindan-5-yl, 1-cis-decahydronaphthyl, 2-cis-decahydronaphthyl, 1-trans-decahydronaphthyl, 2-trans-decahydronaphthyl, exo-2-norbornyl, endo-2-norbornyl, 1-adamantyl; $C_8$–$C_{14}$ polycycloalkylalkyl, e.g., 1-adamantylmethyl; $C_7$–$C_{12}$ polycycloalkenyl, e.g., bicyclo[2.2.1] hept-5-ene-2-yl; $C_8$–$C_{14}$ polycycloalkenylalkyl, e.g., bicyclo[2.2.2]-oct-5-ene-2-ylmethyl; $C_1$–$C_{10}$ alkylthio-$C_{10}$–$C_2$alkyl, e.g., 2-ethylthioethyl, 2-butylthioethyl; aryloxy $C_2$–$C_6$ alkyl, e.g., 2-phenoxyethyl, 4-phenoxybutyl; phenylthio $C_2$–$C_6$ alkyl, e.g., 2-phenylthioethyl; $C_6$–$C_{14}$ aryl, e.g., phenyl, 4-biphenylyl, 1-naphthyl, 5,6,7,8-tetrahydro-1-naphthyl; $C_7$–$C_{14}$ aralkyl, e.g., benzyl, 1-phenylethyl, 2-phenylethyl, $C_9$–$C_{14}$ arylcycloalkyl, e.g., 2-phenylcyclopropyl; $C_9$–$C_{14}$ benzocycloalkyl, e.g., 1-indanyl, 2-indanyl, 1,2,3,4-tetrahydro-1-naphthyl; $C_6$–$C_{14}$ aryl and aralkyl substituted with groups such as loweralkyl, e.g., 2-tolyl, 3-tolyl, 4-tolyl, 2-isopropylphenyl, 4-isopropylphenyl, 4-butylphenyl, 4-hexylphenyl, 2,4-dimethylphenyl, 2,6-dimethylphenyl, 3,5-dimethylphenyl, 2,6-diethylphenyl, 2,6-diisopropylphenyl, 2-ethyl-6-methylphenyl, 2-methyl-6-isopropylphenyl, 2,4,5-trimethylphenyl, 2,4,6-trimethylphenyl, 2-methylbenzyl, 3-methylbenzyl, 4-methylbenzyl; trifluoromethyl, e.g., 2-trifluoromethylphenyl, 3-trifluoromethylphenyl, 4-trifluoromethylphenyl, 3,5-bis(trifluoromethyl)phenyl, 2-trifluoromethylbenzyl, 3-trifluoromethylbenzyl, 4-trifluoromethylbenzyl, 2-(3-trifluoromethylphenyl)ethyl; loweralkoxy, e.g., 2-methoxyphenyl, 4-methoxyphenyl, 4-ethoxyphenyl, 4-butoxyphenyl, 2,4-dimethoxyphenyl; trifluoromethoxy, e.g., 4-trifluoromethoxyphenyl; phenoxy, e.g., 4-phenoxyphenyl; loweralkylthio, e.g., 3-methylthiophenyl, 4-methylthiophenyl, 4-ethylthiophenyl; halo, e.g., 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 4-chloro-1-naphthyl, 2,3-dichlorophenyl, 2,4-dichlorophenyl, 2,6-dichlorophenyl, 3,5-dichlorophenyl, 3,4-dichlorophenyl, 2,4-dibromophenyl, 2,5-difluorophenyl, 2,4,5-trichlorophenyl, 2,4,6-trichlorophenyl, 2,3,4,5-tetrachlorophenyl, 2,3,4,5,6-pentafluorophenyl, 2-chlorobenzyl, 3-chlorobenzyl, 4-chlorobenzyl, 4-fluorobenzyl, 4-bromobenzyl, 2-(4-chlorophenyl)ethyl, 1-(4-chlorophenyl)-ethyl, nitro, e.g., 2-nitrophenyl, 3-nitrophenyl, 4-nitrophenyl, 4-nitrobenzyl; cyano, e.g., 2-cyanophenyl, 3-cyanophenyl, 4-cyanophenyl; alkanoyl, e.g., 2-acetylphenyl, 3-acetylphenyl, 4-acetylphenyl, 4-acetylbenzyl; benzoyl, e.g., 4-benzoylphenyl; loweralkoxycarbonyl, e.g., 2-ethoxycarbonyl, 3-ethoxycarbonyl, 4-ethoxycarbonyl, diloweralkylamino, e.g., 3-dimethylaminophenyl, 4-dimethylaminophenyl, 4-diethylaminophenyl; loweralkylsulfonyl, e.g., 4-butylsulfonylphenyl, 4-methylsulfonylphenyl; fluorosulfonyl, e.g., 3-fluorosulfonylphenyl; loweralkylsulfinyl, e.g., 3-methylsulfinylphenyl, 4-methylsulfinylphenyl; mixed substituents e.g., 4-bromo-2,6-dimethylphenyl, 2-chloro-6-methylphenyl, 5-chloro-2-methylphenyl, 2-chloro-5-trifluoromethylphenyl, 4-chloro-3-trifluoromethylphenyl, 2-chloro-3-nitrophenyl, 2-chloro-4-nitrophenyl, 2-chloro-5-nitrophenyl, 4-chloro-2-nitrophenyl, 2-methoxy-5-methylphenyl, 2-methoxy-4-nitrophenyl, 2-methoxy-5-nitrophenyl, 4-methyl-2-nitrophenyl, 4-methyl-3-nitrophenyl, 3-chloro-4-fluorophenyl, 3-chloro-2-methoxyphenyl, 4-chloro-2-methoxyphenyl, 2-fluoro-3-nitrophenyl, 2-fluoro-5-nitrophenyl, 3-chloro-2-phenoxyphenyl, 3-chloro-2,4-dimethoxyphenyl, 4,5-dimethyl-2-nitrophenyl, 4-methylthio-3-chlorophenyl.

Among these groups the preferred Z groups are $C_4$–$C_{12}$ alkyl, straight chain and branched $C_5$–$C_{10}$ cycloalkyl, $C_6$–$C_{10}$ cycloalkylalkyl, $C_6$–$C_{10}$ cycloalkenylalkyl, phenyl, naphthyl, phenyl $C_1$–$C_4$ alkyl, phenyl $C_3$ cycloalkyl, $C_1$–$C_4$ alkylphenyl, $C_1$–$C_3$ alkylbenzyl, trifluoromethylphenyl, trifluoromethylbenzyl, trifluoromethylphenylethyl, $C_1$–$C_4$ alkoxyphenyl, trifluoromethoxyphenyl, phenoxyphenyl, $C_1$–$C_4$ alkylthiophenyl, halophenyl, halobenzyl, halophenylethyl, $C_1$–$C_4$ acylphenyl, $C_1$–$C_4$ alkoxycarbonylphenyl, $C_1$–$C_4$ alkylsulfonylphenyl, and trifluoromethylphenylethyl. More preferred groups are 2-ethylhexyl, 1,5-dimethylhexyl, 1,3-dimethylpentyl, 1,4-dimethylpentyl, 1,1,3,3-tetramethylbutyl, 1-methylhexyl, cyclohexylmethyl, cycloheptylmethyl, cyclopentylmethyl, 3-cyclohexen-1-ylmethyl, phenyl, 4-tolyl, 1-phenylethyl, 3-trifluoromethylphenyl, 4-trifluoromethylphenyl, 4-ethoxyphenyl, 3-methylthiophenyl, 4-methylthiophenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 4-methylthio-3-chlorophenyl, 1-adamantyl, 2-norbornyl, 1-adamantylmethyl, 1-(4-chlorophenyl)ethyl, 2-(4-chlorophenyl)ethyl, and 2-(3-trifluoromethylphenyl)ethyl.

A preferred genus of Z groups comprises the group consisting of $C_4$–$C_{12}$ alkyl, $C_5$–$C_{10}$ cycloalkyl, $C_6$–$C_{10}$ cycloalkylalkyl, 3-cyclohexen-1-ylmethyl, $C_7$–$C_{10}$ polycycloalkyl, $C_8$–$C_{12}$ polycycloalkylalkyl, phenyl, naphthyl, phenyl $C_1$–$C_4$ alkyl, phenyl $C_3$ cycloalkyl, $C_1$–$C_4$ alkylphenyl, $C_1$–$C_3$ alkylbenzyl, trifluoromethylphenyl, trifluoromethylbenzyl, trifluoromethylphenylethyl, $C_1$–$C_4$ alkoxyphenyl, trifluoromethoxyphenyl, phenoxyphenyl, $C_1$–$C_4$ alkylthiophenyl, halophenyl, halobenzyl, halophenylethyl, $C_2$–$C_4$ alkanoylphenyl, $C_1$–$C_4$ alkoxycarbonylphenyl, and $C_1$–$C_4$ alkylsulfonylphenyl radicals.

By combination of the above described groups, different antimicrobial compounds can be prepared. The preferred compounds are those exhibiting the greatest antimicrobial activity, with longest duration of intraoral residence time and antimicrobial activity. Preferred compounds are those having the formula:

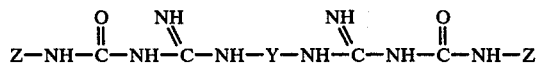

wherein Y is selected from the group consisting of 3-aza-1,5-pentanediyl, 4-methyl-4-aza-1,8-octanediyl, 4-methyl-4-aza-1,7-heptanediyl, 1,4-piperazinediylbis(2,1- ethanediyl), and 1,4-piperazinediylbis(3,1-propanediyl), and Z is selected from the group consisting of 2-ethylhexyl, 1,5-dimethylhexyl, 1,3-dimethylhexyl, 1,4-dimethylpentyl. 1,1,3,3-tetramethylbutyl, 1-methylhexyl, cyclohexylmethyl, cycloheptylmethyl, cyclopentylmethyl, 1-cyclohexylethyl, 2-cyclohexylethyl, 3-cyclohexen-1-ylmethyl, phenyl, 3-trifluoromethylphenyl, 4-trifluoromethylphenyl, 4-ethoxyphenyl, 3-methylthiophenyl, 4-methylthiophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 4-methylthio-3-chlorophenyl, 1-adamantyl, 2-norbornyl, 1-adamantylmethyl, 2-(4-chlorophenyl)ethyl, 1-(4-chlorophenyl)ethyl, 4-chlorobenzyl.

A preferred genus of compounds is that having the formula:

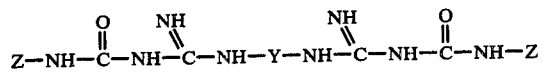

wherein Y is selected from the group consisting of 3-loweralkyl-3-aza-1,5-pentanediyl, 3-loweralkyl-3-aza-1,6-hexanediyl, 5-loweralkyl-5-aza-1,7-heptanediyl, 4-loweralkyl-4-aza-1,8-octanediyl, 7-loweralkyl-7-aza-1,9-nonanediyl 1,4-piperazinediylbis(loweralkanediyl), 1,4-diazacycloheptanediylbis(loweralkanediyl), 1,4-diazacyclooctanediylbis(loweralkanediyl), 1,5-diazacyclooctanediylbis(loweralkanediyl), and Z is selected from the group consisting of $C_4$-$C_{12}$ alkyl, $C_5$-$C_{10}$ cycloalkyl, $C_6$-$C_{10}$ cycloalkylalkyl, 3-cyclohexen-1-ylmethyl, $C_7$-$C_{10}$ polycycloalkyl, $C_8$-$C_{12}$ polycycloalkylalkyl, phenyl, naphthyl, phenyl $C_1$-$C_4$ alkyl, phenyl $C_3$ cycloalkyl, $C_1$-$C_4$ alkylphenyl, $C_1$-$C_3$ alkylbenzyl, trifluoromethylphenyl, trifluoromethylbenzyl, trifluoromethylphenylethyl, $C_1$-$C_4$ alkoxyphenyl, trifluoromethoxyphenyl, phenoxyphenyl, $C_1$-$C_4$ alkylthiophenyl, halophenyl, halobenzyl, halophenylethyl, $C_2$-$C_4$ alkanoylphenyl, $C_1$-$C_4$ alkoxycarbonylphenyl and $C_1$-$C_4$ alkylsulfonylphenyl radicals.

Another preferred genus of compounds is that having the formula:

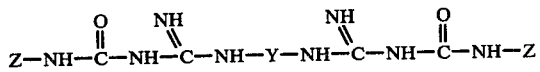

wherein Y is selected from the group consisting of 3-methyl-3-aza-1,5-pentanediyl, 4-methyl-4-aza-1,7-heptanediyl, 5-methyl-5-aza-1,9-nonanediyl, 3,6-dimethyl-3,6-diaza-1,8-octanediyl, 4,7-dimethyl-4,7-diaza-1,10-decanediyl, 1,4-piperazinediylbis(2,1-ethanediyl), 1,4-piperazinediylbis(3,1-propanediyl), 1,4-piperazinediylbis(1-methyl-2,1-ethanediyl), 1,4-piperazinediylbis(2-methyl-2,1-ethanediyl), 1,4-piperazinediylbis(2-methyl-3,1-propanediyl), 1,4-(1,4-diazacycloheptanediyl)-bis(3,1-propanediyl), and Z is selected from the group consisting of 2-ethylhexyl, 1,3-dimethylpentyl, 1,4-dimethylpentyl, 1,5-dimethylhexyl, 1,1,3,3-tetramethylbutyl, 1-methylhexyl, cyclohexylmethyl, cycloheptylmethyl, cyclopentylmethyl, 3-cyclohexen-1-ylmethyl, 1-adamantyl, 2-norbornyl, 1-adamantylmethyl, phenyl, 4-tolyl, 1-phenylethyl, 3-trifluoromethylphenyl, 4-trifluoromethylphenyl, 4-ethoxyphenyl, 3-methylthiophenyl, 4-methylthiophenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 4-methylthio-3-chlorophenyl, 1-(4-chlorophenyl)ethyl, 2-(4-chlorophenyl)ethyl, and 2-(3-trifluoromethylphenyl)ethyl radicals.

It should be understood that the term diloweralkylamino-substituted phenyl includes both compounds wherein the alkyl groups are separate and compounds in which the two alkyl groups attached to the amino nitrogen atom are part of a homocyclic or heterocyclic ring.

It is well known in the pharmacological arts that acid addition salts of pharmacologically active amine compounds do not differ in activities from their free bases. The salts merely provide a convenient solubility factor.

The carbamylguanidino compounds of this invention may be converted to their pharmaceutically acceptable acid addition salts which are equivalent by customary methods in the art. The pharmaceutically acceptable salts of this invention are those salts, the acid component of which is pharmacologically acceptable in the intended dosages. Suitable salts are those prepared from inorganic acids or organic acids. Such acids include, but are not limited to: hydrochloric acid, hydrobromic acid, hydrofluoric acid, nitric acid, sulfuric acid, sulfamic acid, the polyphosphoric acids, phosphoric acid, monofluorophosphoric acid, glycerophosphoric acid, acetic acid, propionic acid, butyric acid, succinic acid, glycolic acid, 2,3-dihydroxypropionic acid, saccharic acid, gluconic acid, lactobionic acid, phenylacetic acid, cyclohexylcarboxylic acid, maleic acid, fumaric acid, lactic acid, citric acid, malic acid, camphoric acid, benzoic acid, tartaric acid, aspartic acid, salicyclic acid, phthalic acid, methanesulfonic acid, ethanesulfonic acid, benzenesulfonic acid, toluenesulfonic acid, nicotinic acid, ascorbic acid and the like. Preferred acids are hydrochloric, acetic, gluconic, and methanesulfonic.

Another preferred genus of acids comprises the group consisting of hydrochloric acid, hydrobromic acid, nitric acid, sulfuric acid, acetic acid, glycolic acid, 2,3-dihydroxypropionic acid, saccharic acid, gluconic acid, lactobionic acid, maleic acid, fumaric acid, tartaric acid, lactic acid, citric acid, malic acid, methanesulfonic acid, ethanesulfonic acid, and ascorbic acid.

Compounds containing the carbamylguanidino or thiocarbamylguanidino group can be prepared by the general reaction of an organic isocyanate or isothiocyanate with a substituted guanidine according to the following general reaction scheme:

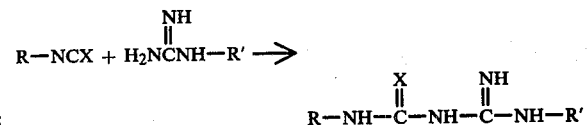

wherein R and R' represent organic radicals and X represents oxygen or sulfur.

The procedure for carrying out this reaction is described in Curd, J. Chem. Soc., 1949, 1732–1738.

To prepare a bis-carbamylguanidino compound according to this invention of the type:

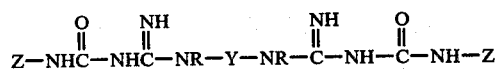

one mole of a bis-guanidino compound of the formula:

is reacted with two moles of an isocycnate having the formula:

Z-NCO by the procedure specified above. The corresponding compound having sulfur in place of oxygen, i.e., a compound having the formula:

is prepared analogously by reacting two moles of an isothiocyanate of the formula Z-NCS with one mole of a bis-guanidino compound. The isothiocyanate can be prepared from the corresponding isocyanate by reaction with O, O'-diethyldithiophosphate according to the process disclosed in U.S. Patent 3,409,656.

When a compound of the formula:

is to be prepared, one mole of a suitable diisocycnate of the formula:

OCN—Y—NCO is reacted with two moles of a guanidine of the formula:

under the conditions specified above. Likewise, the analogous compound containing sulfur in place of oxygen, i.e., having the formula:

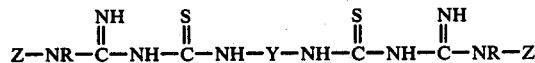

can be prepared by the same procedure using a diisothiocyanate in place of the diisocyanate.

Since both guanidines and isocyanates can be easily prepared from the corresponding amino compounds, the novel compounds of this invention may be synthesized from suitable readily available amines by standard methods. In one common synthetic procedure, amino groups are converted to a isocyanate groups by reaction with phosgene, COCl$_2$. A particular synthesis for the preparation of diisocyanates by this reaction is given in British Pat. No. 901,337. Other syntheses, such as the thermal rearrangement of azides of carboxylic acids (Curtius rearrangement) and thermal decomposition or base catalyzed decomposition of urethanes, ureas, and the like can also be used to prepare the required isocyanates.

The guanidines or bis-guanidines required for synthesizing the compounds of this invention may be prepared from the corresponding amines by the well-known reaction with sodium cyanamide or by reaction with S-methylisothiourea sulfate according to the process described in Heyn, U.S. Pat. No. 1,737,192.

Thus the synthesis of compounds of either the formula:

or the formula:

from readily available amines and diamines can be illustrated by the following scheme:

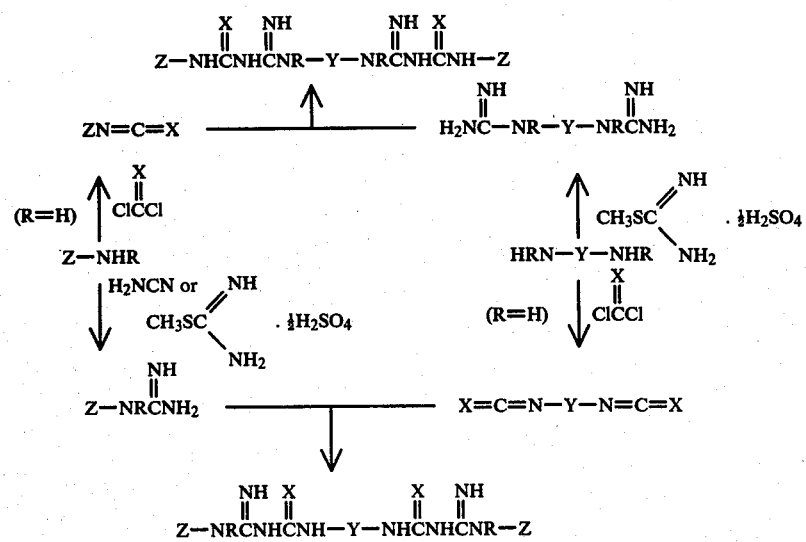

A preferred method of synthesizing those compounds wherein Z is an aliphatic, alicyclic, or substituted aliphatic or alicyclic group is that disclosed in the application by Ronald A. Wohl, filed of even date. In order to synthesize, by that process, compounds having the formula:

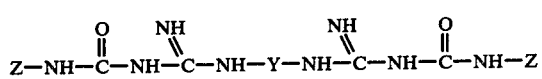

two moles of an S-alkyl isothiobiuret, e.g., a 4-methyl-4-isothiobiuret having the formula:

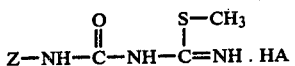

wherein A is the anion of an acid, are reacted with one mole of a diamine having the formula:

H₂N—Y—NH₂ according to the equation:

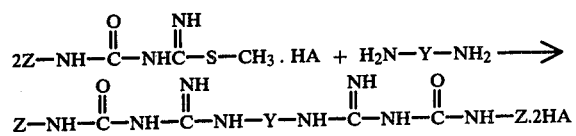

The reaction can be conveniently carried out contacting the reagents in a suitable solvent at a temperature between 20° C. and 100° C. Suitable solvents include alcohols, preferably methanol, water-alcohol mixtures, nitromethane, acetonitrile, and the like. While the above reaction uses the acid addition salt of the isothiobiuret, the free base form may also be used. The isothiobiuret reagent may be prepared by known procedures, e.g., by reacting an isocyanate of the formula:

Z—N=C=O with an S-methyl-isothiourea of the formula:

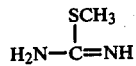

according to the equation:

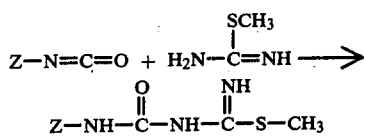

This reaction is conveniently carried out by the procedure described in German Offenlegungsschrift 2,326,312, published December 06, 1973. Thus the synthesis of the compounds of this invention via the isothiobiuret intermediates, starting from amines and using well-known reagents and processes may be illustrated by the following scheme:

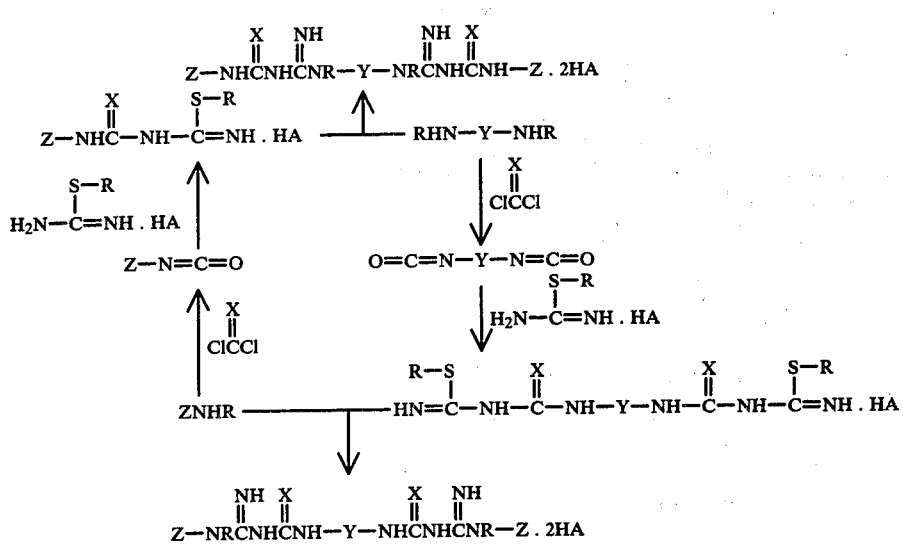

The reaction of substituted cyanoureas with diamines can also be used to prepare compounds of this invention of the formula:

Z—NH—C(=O)—NH—C(=NH)—NR—Y—NR—C(=NH)—NH—C(=O)—NH—Z

Thus if two moles of a substituted cyanourea of the formula:

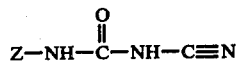

are reacted with one mole of a diamine dihydrochloride of the formula:

HRN—Y—NHR.2HCl compounds of the above-described type can be obtained.

It will be understood by the skilled practitioner that when a polyamine having two primary amino groups and one or more secondary amino groups is to be converted into a compound of this invention by the procedure outlined above, mixtures of compounds may be formed. Hence, it may be necessary to separate the desired bis-guanidines and bis-carbamylguanidines from undesired by-products formed by reaction of the secondary amino groups with the reagent. This separation may be performed by well-known techniques such as fractional crystallization or chromatography.

Alternatively, the aza groups may be protected from reaction with ZNCO or ZNCS by bonding to them a protective group which can be easily removed after the terminal amino groups have been reacted according to the above scheme. The protective group may be any of those which are commonly used to temporarily protect secondary amino groups, e.g., benzyl, acetyl, or carbobenzoxy. The particular protective group chosen must, of course, be stable toward all reactions used in a particular synthetic procedure. The protective group may be attached to the aza groups by reacting a precursor of the protective group with a suitable polyamine after the terminal amine groups have been blocked by reaction with a blocking group. When the terminal amino groups are primary amino groups, a phthalimido group, which is specific for blocking primary amines, may be used under conditions known in the art. After the aza groups have been protected, the terminal amino groups can be regenerated by removing their blocking groups and the synthesis can be carried out as outlined above. After the synthesis has been completed, the aza groups are regenerated by removing the protective groups by means known in the art, e.g., by catalytic hydrogenation. The introduction and removal of protective groups for amines is described in standard texts, e.g., J. F. W. McOmie, Protective Groups in Organic Chemistry, Plenum Press., New York, 1973. Thus the synthesis of a compound of this invention by this procedure might proceed as follows:

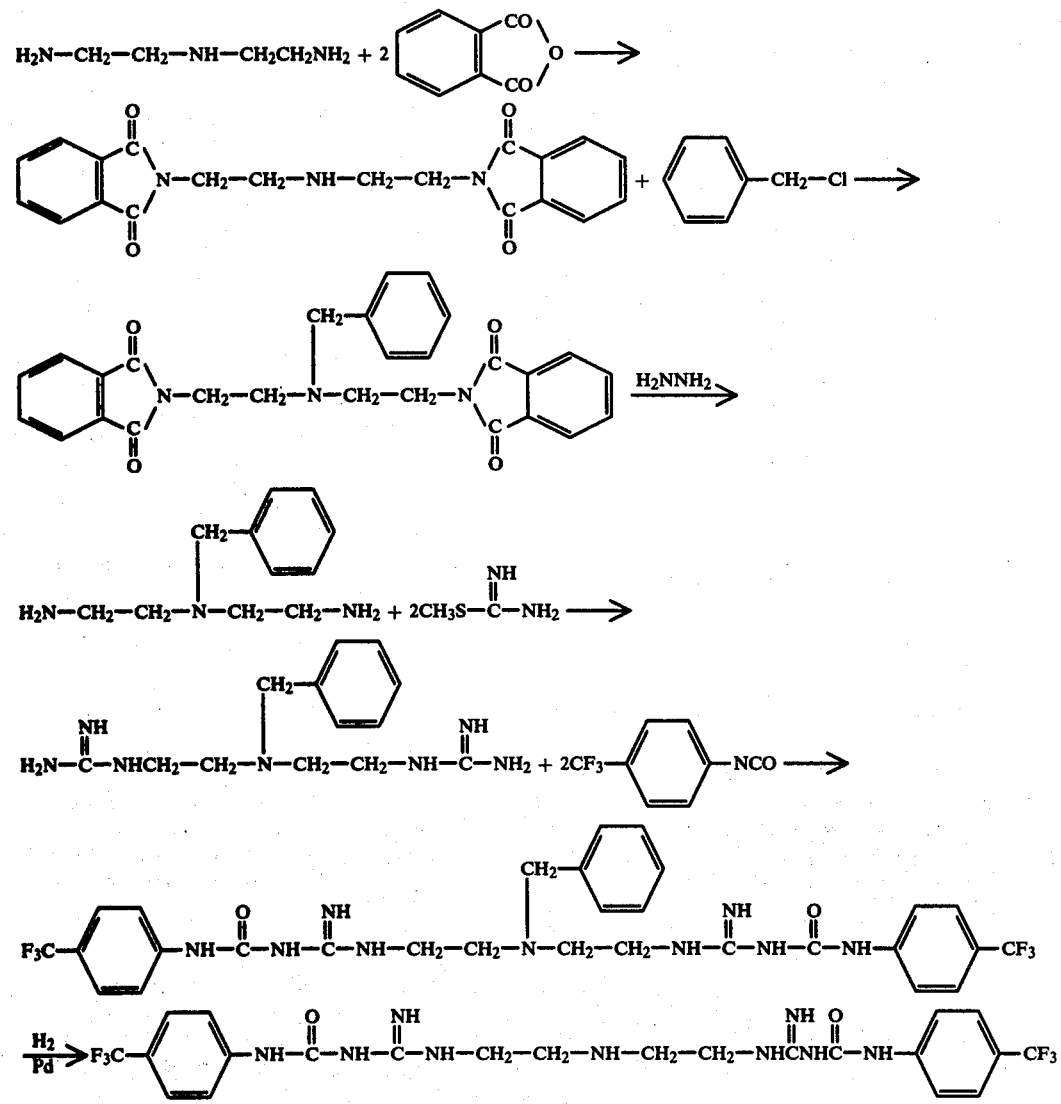

In an alternative procedure, the polyamine having the aza groups protected may be synthesized directly from an amine incorporating the protective groups. For example, the following reaction sequence may be used.

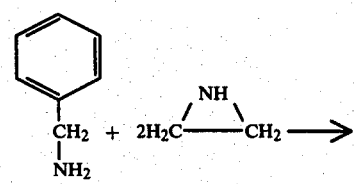

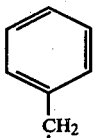
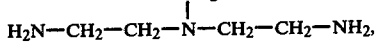

The resulting polyamine may then be used to prepare the corresponding carbamylguanidine by the reaction scheme outlined above, and the benzyl group may be removed by catalytic hydrogenation to yield a compound according to this invention.

When a compound of the invention having a cyclic diamino skeleton in the Y group is desired, the appropriate polyamine starting material can be reacted with a suitable halonitrile or unsaturated nitrile to form a N,N'-bis-alkyl nitrile compound which can subsequently be converted to the polyamine by catalytic hydrogenation. Thus, the following reaction sequence may be used to prepare a typical cyclic polyamine.

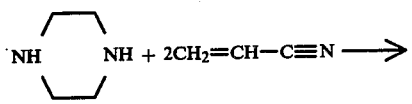

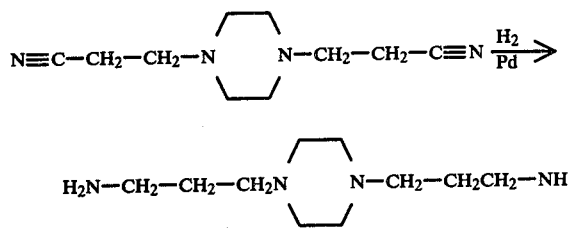

Suitable procedures for preparing polyamines of this type may be found in Mull, R. P.; Mizzoni, R. H.; Dapero, M. R.; and Egbert, M. E., J. Med. Pharm. Chem., 5, 944–949 (1962) and in Behr, L. C.; Kirby, J. E.; McDonald, R. N.; and Todd, C. W., J. Am. Chem. Soc., 68, 1296–1297 (1946). When polyamines of this type are used as starting materials for preparing compounds of this invention, no protecting groups need be used, since besides the terminal amino groups which enter into the reaction only tertiary amino groups, which do not carry active hydrogen, are present in the polyamine.

Likewise, when a compound of this invention having an open chain Y group containing only tertiary amino groups within the chain, e.g., —CH$_2$—CH$_2$—N(CH$_3$)—CH$_2$—CH$_2$—, is to be prepared, a suitable polyamine having terminal primary or secondary amino groups and internal tertiary amino groups is used as a starting material. Since the tertiary amino groups are devoid of active hydrogen, they will not react with the reagents used in the general synthesis outlined above. Hence the synthesis of compounds of the invention of this type is straightforward and without complication.

The open chain polyamines, terminated with primary or secondary amino groups, which serve as starting materials for the synthesis of the compounds of this invention, may be prepared by conventional means. For example, amines of the formula

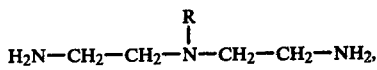

wherein R is an alkyl group may be prepared by condensing two moles of ethyleneimine with a primary amine having the formula RNH$_2$. Similarly, primary amines may be condensed with appropriate halonitriles such as ClCH$_2$CN or Cl—CH$_2$—CH$_2$—C≡N or Cl—CH$_2$—CH$_2$—CH$_2$—C≡N, or acrylonitrile or methacrylonitrile and the condensation product catalytically hydrogenated to yield polyamines having 2 or 3 or 4 carbon atoms between the amino groups. In similar fashion, by means well-known to those skilled in the art, the unsymmetrical polyamines may be prepared. For example, a reaction such as the following may be employed:

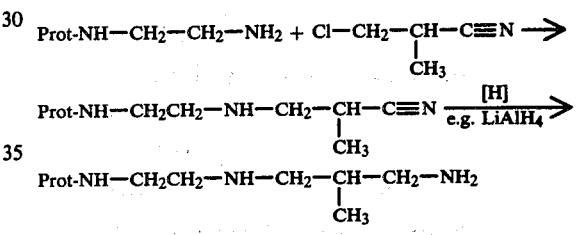

wherein Prot is a conventional amine protecting group which is removed after the synthesis is completed.

Amines of the type 1,1'-ethylenebis[4-(2-aminoethyl)-piperazine], having the structural formula:

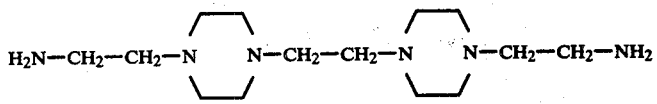

may be prepared by reacting 1,1'-ethylenedipiperazine, having the structural formula:

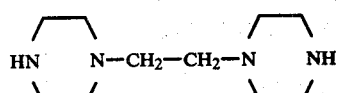

(prepared according to the procedures of U.S. Pat. No. 2,943,135) with chloroacetonitrile to form 1,1'-ethylenebis(4-cyanomethylpiperazine), having the structural formula:

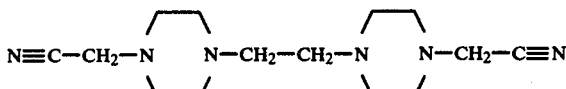

followed by catalytic reduction as outlined above to form the desired amine.

The acid addition salts of the novel compounds are prepared by adding a solution containing an equivalent amount of the corresponding acid to a solution of the compound.

The equivalent amount is determined by the number of ionizable hydrogen atoms present in the acid, and the salt that is desired. The novel compounds of this invention contain three or more basic sites in the molecule any or all of which may react with the ionizable hydrogen atoms of the acid. Thus, one or more moles of a monobasic acid such as hydrochloric acid, acetic acid, or gluconic acid may react with one mole of the novel compound to form the mono-, tri- or higher salt respectively. Likewise, one-half mole, one mole or more of a dibasic acid such as sulfuric acid or succinic acid may react with one mole of the bis-carbamylguanidine. Again, a tribasic acid such as phosphoric acid or citric acid, may combine in proportions of 1/3, 1/2, 2/3, 1, 4/3, 3/2, 5/3, 2 or 3 moles of acid to one mole of bis-carbamylguanidine, depending on the total number of amino groups in the molecule. It will be understood by one skilled in the art that the actual salts formed under particular conditions will depend upon the ionization constants of the acids and bases and the mole ratio in which they are present.

Particularly preferred salts are those containing several anions such as the trimethanesulfonates and trigluconates of compounds having three basic groups and the tri- and tetramethanesulfonates and tri- and tetragluconates of compounds having four basic groups.

The antimicrobial activity of the compounds of the invention is determined by the following in vitro assays:

A zone of inhibition test is performed by placing a 1/4" diameter filter paper disk wet with an aqueous solution of the test compound of the chosen concentration on a brain-heart infusion or tripticase soy agar plate seeded with the microorganism to be inhibited. The plate is incubated at 37° C. for 24 hours and the diameter of the zone around the filter paper in which growth of the microorganism has been inhibited is measured. The greater the diameter of the zone of inhibition, the more effective is the compound against the particular microorganism. This test may also be run with the medium diluted with an equal volume of water.

A quantitative serial dilution test may also be performed by the following procedure.

A 20 mg/ml solution of the compound to be tested is prepared in a standard brain-heart infusion broth medium which has been diluted with water to one-half standard strength.

Serial dilutions are prepared by adding 1 ml of the solution to a test tube containing 9 ml of medium. Five milliliters of the resulting solution are then added to another test tube containing 5 ml of the medium. The resulting solution is then again diluted by the same procedure. Ordinarily one tenfold dilution and four twofold dilutions are made. The procedure can be continued if more dilute solutions are required. Each of the series of tubes containing solutions of the compounds to be assayed is inoculated with two drops of a heavy culture of the chosen microorganisms in the brain-heart infusion broth. The tubes are incubated at 37° C. for 36 hours and the most dilute solution showing no microbial growth is noted. The concentration of this solution is reported as the minimal inhibitory concentration (MIC).

The compounds of this invention are useful antimicrobials against such microorganisms as S. mutans, A. viscosus, and A. naeslundi, Staph. aureus, E. Coli, Ps. aeruginosa and C. albicans.

Acute oral toxicity of the compounds of this invention is determined in mice by the following procedure. The mice are fasted overnight, then formed into groups of 10 for testing. The animals in each group are fed a chosen dose and the dose is varied from group to group to cover a range of doses. The groups are then observed for a period of five days and the number of dead animals in each group is noted each day. The $LD_{50}$ is calculated from this data according to the method of Weil, Biometrics, 8(3), 249 263 (1952).

The compounds of this invention show a low order of acute oral toxicity.

The taste of compounds of this invention may be evaluated by standard taste panels. The compounds of this invention are devoid of the extremely bitter taste associated with chlorhexidine and do not alter taste perception after rinsing the mouth at the concentration useful for microbial inhibition.

The novel compounds of this invention are useful as topical antimicrobial agents. Suitable concentrations of these compounds for topical application to exert their antimicrobial activities are in the range of 0.1% to 5%, preferably 0.5% to 1%.

The antimicrobial compounds of this invention can be administered into the oral cavity to reduce the numbers of plaque-forming bacteria in the mouth. They can be added to toothpastes, tooth powders, mouthwashes, and the like so as to constitute from 0.1% to 2% of the composition.

A suitable method of treatment is to apply to the teeth once or twice a day a solution having a concentration of 0.1% to 2% preferably 0.2% to 1% of a carbamylguanidino compound of this invention. Such a treatment has been found to significantly reduce the numbers of plaque-forming bacteria in the mouths of experimental animals.

In in vivo tests the compounds of this invention substantially reduced the number of S. Mutans in the mouths of hamsters infected with this organism for periods up to 6 hours after a single administration. Repeated daily administration further enhances the intraoral antimicrobial activity of these compound.

The invention will be further illustrated by the following examples which are not, however, intended to limit its scope.

EXAMPLE I 1,7-bis-(p-chlorophenylcarbamylamidino)-1,4-dimethyl-1,4,7-triazaheptane trihydrochloride This example illustrates the synthesis of a compound of this invention having a straight chain nitrogen-containing group.

One gram (0.04 moles) of sodium was dissolved in 100 ml of acetone. To this solution was added 6 grams of N-[2-(1-methylguanidino)ethyl]-N-(2-guanidinoethyl)-methylamine sulfate and the mixture was stirred for one hour and 20 minutes. To this mixture was added 6.2 grams (0.04 moles) of 4-chlorophenylisocyanate. The resulting mixture was stirred overnight, heated to reflux temperature for four hours, cooled, the precipitated sodium sulfate filtered, and the filtrate concentrated by distilling off the acetone under vacuum, and then poured into water. An oily material was formed which was separated from the water by decantation, and triturated with diethyl ether. The solid was dissolved in 30 milliliters of chloroform, dried over anhydrous sodium sulfate, and hydrogen chloride gas was bubbled through the solution until it became acidic. The solvent was removed by evaporation under vacuum, the residue was triturated with anhydrous diethyl ether, and the trihydrochloride salt of the product collected on a filter. M.P. 220°–225° C. (dec.).

EXAMPLE II 1,4-Bis[3-(4-chlorophenylcarbamylguanidino)propyl]-piperazine

This example illustrates the synthesis of a compound of this invention having a heterocyclic ring in the Y radical.

N,N'-Bis-(3-aminopropyl)piperazine (20 g, 0.1 mole) was dissolved in warm water and added dropwise to a warm aqueous solution of 2-methyl-2-thiopseudourea sulfate (27.8 g, 0.1 mole) with stirring. The mixture was stirred for 5 hours and the precipitate which formed was collected on a filter, washed with cold water, and recrystallized from water.

Sodium (1 g, 0.04 mole) was dissolved in acetone with cooling under a nitrogen atmosphere. To this solution was added N,N'-bis-(3-guanidinopropyl)piperazine sulfate (7.65) g, 0.02 mole) was added and the mixture was stirred for two hours. 4-Chlorophenyl isocyanate (6.1 g, 0.04 mole) was then added and the mixture was stirred overnight. The mixture was then heated to reflux temperature for one hour, cooled, and the solid precipitate of sodium sulfate removed by filtration. The solvent was removed from the filtrate and the solid residue was triturated twice with water. The residue was then triturated twice with diethyl ether and collected on a filter. M.P. 199°–202° C. (dec.).

The trimethanesulfonate salt was prepared by adding methanesulfonic acid (0.169 ml, 0.00255 mole) and the compound formed above (0.50 g, 0.00085 mole) to 50 ml of water and stirring the mixture overnight. The solution was filtered to give a clear pale yellow aqueous solution of the trimethanesulfonate salt.

The dimethanesulfonate salt was prepared by suspending the free base (0.500 g, 0.00085 mole) in ethanol and adding methanesulfonic acid (0.163 g, 0.0017 mole). The mixture was stirred for 1.5 hours. The mixture contained a suspended solid which was collected on a filter and washed with ethanol. M.P. 195°–198° C.

EXAMPLE III

This example illustrates the synthesis of several carbamylguanidine compounds of this invention.

When the procedures of Example II are followed using the reagents listed in Table I, the corresponding compounds listed in Table I are prepared.

TABLE I

| Reagents | | |
|---|---|---|
| Isocyanate | Bis-guanidine | Product |
| 4-chlorophenyl isocyanate | 1,5-bisguanidino-3-azapentane | 1,5-bis(4-chlorophenylcarbamylguanidino)-3-azapentane |
| 4-chlorophenyl isocyanate | 1,5-bisguanidino-3-methyl-3-azapentane | 1,5-bis(4-chlorophenylcarbamylguanidino)-3-methyl-3-azapentane |
| 4-chlorophenyl isocyanate | 1,5-bisguanidino-3-ethyl-3-azapentane | 1,5-bis(4-chlorophenylcarbamylguanidino)-3-ethyl-3-azapentane |
| 4-chlorophenyl isocyanate | 1,5-bisguanidino-3-allyl-3-azapentane | 1,5-bis(4-chlorophenylcarbamylguanidino)-3-allyl-3-azapentane |
| 4-chlorophenyl isocyanate | 1,5-bisguanidino-3-propargyl-3-azapentane | 1,5-bis(4-chlorophenylcarbamylguanidino)-3-propargyl-3-azapentane |
| 4-chlorophenyl isocyanate | 1,5-bisguanidino-3-cyclohexyl-3-azapentane | 1,5-bis(4-chlorophenylcarbamylguanidino)-3-cyclohexyl-3-azapentane |
| 4-chlorophenyl isocyanate | 1,5-bisguanidino-3-benzyl-3-azapentane | 1,5-bis(4-chlorophenylcarbamylguanidino)-3-benzyl-3-azapentane |
| 4-chlorophenyl isocyanate | 1,6-bisguanidino-3-azahexane | 1,6-bis(4-chlorophenylcarbamylguanidino)-3-azahexane |
| 4-chlorophenyl isocyanate | 1,7-bisguanidino-4-azaheptane | 1,7-bis(4-chlorophenylcarbamylguanidino)-4-azaheptane |
| 4-chlorophenyl isocyanate | 1,7-bisguanidino-4-methyl-4-azaheptane | 1,7-bis(4-chlorophenylcarbamylguanidino)-4-methyl-4-azaheptane |
| 4-chlorophenyl isocyanate | 1,5-bisguanidino-2,3,4-trimethyl-3-azapentane | 1,5-bis(4-chlorophenylcarbamylguanidino)-2,3,4-trimethyl-3-azapentane |
| 4-chlorophenyl isocyanate | 1,9-bisguanidino-5-methyl-5-azanonane | 1,9-bis(4-chlorophenylcarbamylguanidino)5-methyl-5-azanonane |
| 4-chlorophenyl isocyanate | 1,8-bisguanidino-3,6-diazaoctane | 1,8-bis(4-chlorophenylcarbamylguanidino)3,6-diazaoctane |
| 4-chlorophenyl isocyanate | 1,8-bisguanidino-3,6-dimethyl-3,6-diazaoctane | 1,8-bis(4-chlorophenylcarbamylguanidino)-3,6-dimethyl-3,6-diazaoctane |
| 4-chlorophenyl isocyanate | 1,11-bisguanidino-4,8-diazaundecane | 1,11-bis(4-chlorophenylcarbamylguanidino)-4,8-diazaundecane |
| 4-chlorophenyl isocyanate | 1,11-bisguanidino-4,8-dimethyl-4,8-diazaundecane | 1,11-bis(4-chlorophenylcarbamylguanidino)-4,8-dimethyl-4,8-diazaundecane |
| 4-chlorophenyl isocyanate | 1,11-bisguanidino-3,6,9-triaza- | 1,11-bis(4-chlorophenylcarbamylguanidino)- |

TABLE I-continued

| Isocyanate | Bis-guanidine | Product |
|---|---|---|
| | undecane | 3,6,9-triazaundecane |
| 4-chlorophenyl isocyanate | 1,4-bis(2-guanidinoethyl)piperazine | 1,4-bis[2-(4-chlorophenylcarbamylguanidino)-ethyl]piperazine |
| 4-chlorophenyl isocyanate | 1,4-bis(2-guanidinoethyl)-1,4-diazepine | 1,4-bis[2-(4-chlorophenylcarbamylguanidino-ethyl]-1,4-diazepine |
| 4-chlorophenyl isocyanate | 1,4-bis(4-guanidinobutyl)piperazine | 1,4-bis[4-(4-chlorophenylcarbamylguanidino)-butyl]piperazine |
| 4-bromophenyl isocyanate | 1,5-bisguanidino-3-methyl-3-azapentane | 1,5-bis(4-bromophenylcarbamylguanidino)-3-methyl 3-azapentane |
| 2-chlorophenyl isocyanate | 1,4-bis(3-guanidinopropyl)-piperazine | 1,4-bis[3-(2-chlorophenylcarbamylguanidino)-propyl]piperazine |
| 3-trifluoromethylphenyl-isocyanate | 1,4-bis(3-guanidinopropyl)-piperazine | 1,4-bis[3-trifluoromethylphenylcarbamyl-guanidino)propyl]piperazine |
| phenyl isocyanate | 1,4-bis(3-guanidinopropyl)-piperazine | 1,4-bis[3-(phenylcarbamylguanidino)propyl]-piperazine |
| 4-fluorophenyl isocyanate | 1,4-bis(3-guanidinopropyl)-piperazine | 1,4-bis[3-(4-fluorophenylcarbamylguanidino)-propyl]piperazine |
| 4-tolyl isocyanate | 1,4-bis(3-guanidinopropyl)-piperazine | 1,4-bis[3-(4-tolylcarbamylguanidino)propyl]-piperazine |
| 2,6-diethylphenyl isocyanate | 1,4-bis(3-guanidinopropyl)-piperazine | 1,4-bis[3-(2,6-diethylphenylcarbamylguanidino)-propyl]piperazine |
| 3,4-dichlorophenyl isocyanate | 1,4-bis(3-guanidinopropyl)-piperazine | 1,4-bis[3-(3,4-dichlorophenylcarbamyl-guanidino)propyl] piperazine |
| 4-butoxyphenyl isocyanate | 1,4-bis(3-guanidinopropyl)-piperazine | 1,4-bis[3-(4-butoxyphenylcarbamylguanidino)-propyl]piperazine |
| 4-trifluoromethoxyphenyl isocyanate | 1,4-bis(3-guanidinopropyl)-piperazine | 1,4-bis[3-(4-trifluoromethoxyphenylcarbamyl-guanidino)propyl]piperazine |
| 4-butylthiophenyl isocyanate | 1,4-bis(3-guanidinopropyl)-piperazine | 1,4-bis[3-(4-butylthiophenylcarbamylguanidino)-propyl]piperazine |
| 4-bromophenyl isocyanate | 1,4-bis(3-guanidinopropyl)-piperazine | 1,4-bis[3-(4-bromophenylcarbamylguanidino)-propyl]piperazine |
| 4-butylsulfonylphenyl isocyanate | 1,4-bis(3-guanidinopropyl)-piperazine | 1,4-bis[3-(4-butylsulfonylphenylcarbamyl-guanidino)propyl]piperazine |
| heptyl isothiocyanate | 1,4-bis(3-guanidinopropyl)-piperazine | 1,4-bis[3-(heptylthiocarbamylguanidino)-propyl]piperazine |
| benzyl isothiocyanate | 1,4-bis(3-guanidinopropyl)-piperazine | 1,4-bis[3-(benzylthiocarbamylguanidino)-propyl]piperazine |
| 4-chlorophenyl isothiocyanate | 1,4-bis(3-guanidinopropyl)-piperazine | 1,4-bis[3-(4-chlorophenylthiocarbamyl-guanidino)propyl]piperazine |
| 3-trifluoromethylphenyl isothiocyanate | 1,4-bis(3-guanidinopropyl)-piperazine | 1,4-bis[3-(3-trifluoromethylphenylthio-carbamylguanidino)propyl]piperazine |
| 1-naphthyl isocyanate | 1,4-bis(3-guanidinopropyl)-piperazine | 1,4-bis[3-(1-naphthylcarbamylguanidino)-propyl]piperazine |
| 4-chlorophenyl isocyanate | 1,4-bis(1-methyl-2-guanidinoethyl)-piperazine | 1,4-bis[2-(4-chlorophenylcarbamylguanidino)-1-methylethyl]piperazine |
| 4-chlorophenyl isocyanate | 1,4-bis(2-methyl-2-guanidinoethyl)-piperazine | 1,4-bis[2-(4-chlorophenylcarbamylguanidino)-2-methylethyl]piperazine |
| 4-chlorophenyl isocyanate | 1,4-bis(4-guanidinobutyl)-piperazine | 1,4-bis[4-(4-chlorophenylcarbamylguanidino)-butyl]piperazine |

EXAMPLE IV 1,4-bis[3-(1-adamantylcarbamylguanidino)propyl]piperazine dihydrochloride 1.750 grams (5.76 mmole) of 1-(1-adamantyl)-4-methyl-4-isothiobiuret hydrochloride and 0.571 g of 1,4-bis(3-aminopropyl)piperazine were dissolved in 5 ml of methanol and allowed to stand at room temperature overnight. A precipitate formed which was filtered off and washed successively with isopropyl alcohol, isopropyl alcohol-diethyl ether mixture, and diethyl ether. Yield 1.4 g (68%) m.p., 176°–179° C.

EXAMPLE V

This example illustrates the synthesis of other compounds of this invention.

Following the procedure of Example IV the compounds listed in Table II were prepared by reacting the reagents listed in the table.

TABLE II

| ISOTHIOBIURET | DIAMINE | PRODUCT |
|---|---|---|
| 1-(n-octyl)-4-methyl-4-isothiobiuret hydrochloride | 1,4-bis(3-aminopropyl)piperazine | 1,4-bis[3-(n-octylcarbamylguanidino)-propyl]piperazine dihydrochloride |
| 1-(2-ethylhexyl)-4-methyl-4-isothiobiuret hydrochloride | 1,4-bis(3-aminopropyl)piperazine | 1,4-bis[3-(2-ethylhexylcarbamylguanidino)-propyl]piperazine dihydrochloride |
| 1-(1,1,3,3-tetramethylbutyl)-4-methyl-4-isothiobiuret hydrochloride | 1,4-bis(3-aminopropyl)piperazine | 1,4-bis[3-(1,1,3,3-tetramethylbutyl carbamylguanidino)propyl]piperazine dihydrochloride |
| 1,4-dimethyl-4-isothiobiuret hydrochloride | 1,4-bis(3-aminopropyl)piperazine | 1,4-bis[3-(methylcarbamylguanidino)propyl] piperazine dihydrochloride |
| 1-dodecyl-4-methyl-4-isothiobiuret hydrochloride | 1,4-bis(3-aminopropyl)piperazine | 1,4-bis 3-(dodecylcarbamylguanidino)propyl] piperazine dihydrochloride |
| 1-(1,5-dimethylhexyl)-4-methyl-4-isothio- | 1,4-bis(3-aminopropyl)piperazine | 1,4-bis[3-(1,5-dimethylhexylcarbamylguanidino) |

TABLE II-continued

REAGENTS

| ISOTHIOBIURET | DIAMINE | PRODUCT |
|---|---|---|
| biuret hydrochloride | | propyl]piperazine dihydrochloride |
| 1-(1,3-dimethylpentyl)-4-methyl-4-isothiobiuret hydrochloride | 1,4-bis(3-aminopropyl)piperazine | 1,4-bis[3-(1,3-dimethylpentylcarbamylguanidino)propyl]piperazine dihydrochloride |
| 1-(1,4-dimethylpentyl)-4-methyl-4-isothiobiuret hydrochloride | 1,4-bis(3-aminopropyl)piperazine | 1,4-bis[3-(1,4-dimethylpentylcarbamylguanidino)propyl]piperazine dihydrochloride |
| 1-(1-methylhexyl)-4-methyl-4-isothiobiuret hydrochloride | 1,4-bis(3-aminopropyl)piperazine | 1,4-bis[3-(1-methylhexylcarbamylguanidino)propyl]piperazine dihydrochloride |
| 1-(9-decenyl)-4-methyl-4-isothiobiuret hydrochloride | 1,4-bis(3-aminopropyl)piperazine | 1,4-bis[3-(9-decenylcarbamylguanidino)propyl]piperazine dihydrochloride |
| 1-(3-butynyl)-4-methyl-4-isothiobiuret hydrochloride | 1,4-bis(3-aminopropyl)piperazine | 1,4-bis[3-(3-butynylcarbamylguanidino)propyl]piperazine dihydrochloride |
| 1-cyclohexyl-4-methyl-4-isothiobiuret methanesulfonic acid salt | 1,4-bis(3-aminopropyl)piperazine | 1,4-bis[3-(cyclohexylcarbamylguanidino)propyl]piperazine dimethanesulfonic acid salt |
| 1-cyclohexylmethyl-4-methyl-4-isothiobiuret hydrochloride | 1,4-bis(3-aminopropyl)piperazine | 1,4-bis[3-(cyclohexylmethylcarbamylguanidino)propyl]piperazine dihydrochloride |
| 1-(4-chlorobenzyl)-4-isothiobiuret hydrochloride | 1,4-bis(3-aminopropyl)piperazine | 1,4-bis[3-(4-chlorobenzylcarbamylguanidino)propyl]piperazine dihydrochloride |
| 1-[2-(4-chlorophenyl)ethyl]-4-methyl-4-isothiobiuret hydrochloride | 1,4-bis(3-aminopropyl)piperazine | 1,4-bis[3-(2-(4-chlorophenyl)ethylcarbamylguanidino)propyl]piperazine dihydrochloride |
| 1-[1-(4-chlorophenyl)ethyl]-4-methyl-4-isothiobiuret hydrochloride | 1,4-bis(3-aminopropyl)piperazine | 1,4-bis[3-(1-4-chlorophenyl)ethylcarbamylguanidino)propyl]piperazine dihydrochloride |
| 1-[2-(4-chlorophenyl-1,1-dimethyl)ethyl]-4-methyl-4-isothiobiuret hydrochloride | 1,4-bis(3-aminopropyl)piperazine | 1,4-bis[3-(2-(4-chlorophenyl-1,1-dimethyl)ethylcarbamylguanidino)propyl]piperazine dihydrochloride |
| 1-(3-trifluoromethylbenzyl)-4-methyl-4-isothiobiuret hydrochloride | 1,4-bis(3-aminopropyl)piperazine | 1,4-bis[3-(3-trifluoromethylbenzyl,carbamylguanidino)propyl]piperazine dihydrochloride |
| 1-(3-cyclohexen-1-ylmethyl)-4-methyl-4-isothiobiuret hydrochloride | 1,4-bis(3-aminopropyl)piperazine | 1,4-bis[3-(3-cyclohexen-1-ylmethyl)carbamylguandino)propyl]piperazine dihydrochloride |
| 1-(2-norbornyl)-4-methyl-4-isothiobiuret hydrochloride | 1,4-bis(3-aminopropyl)piperazine | 1,4-bis[3-(2-norbornylcarbamylguanidino)propyl]piperazine dihydrochloride |
| 1-(1-adamantyl)-4-methyl-4-isothiobiuret methanesulfonic acid salt | 1,4-bis(3-aminopropyl)piperazine | 1,4-bis[3-(1-adamantylcarbamylguanidino)propyl]piperazine dimethanesulfonic acid salt |
| 1-(1-adamantylmethyl)-4-methyl-4-isothiobiuret hydrochloride | 1,4-bis(3-aminopropyl)piperazine | 1,4-bis[3-(1-adamantylmethylcarbamylguanidino)propyl]piperazine dihydrochloride |
| 1(1,2,3,4-tetrahydro-1-naphthyl)-4-methyl-4-isothiobiuret hydrochloride | 1,4-bis(3-aminopropyl)piperazine | 1,4-bis[3-((1,2,3,4-tetrahydro-1-naphthyl)carbamylguanidino)propyl]piperazine dihydrochloride |
| 1-(4-chlorophenyl)-4-methyl-4-isothiobiuret hydrochloride | 1,4-bis(3-aminopropyl)piperazine | 1,4-bis[3-(4-chlorophenylcarbamylguanidino)propyl]piperazine dihydrochloride |
| 1-benzyl-4-methyl-4-isothiobiuret hydrochloride | 1,4-bis(3-aminopropyl)piperazine | 1,4-bis[3-(benzylcarbamylguanidino)propyl]piperazine dihydrochloride |
| 2-indanyl-4-methyl-4-isothiobiuret hydrochloride | 1,4-bis(3-aminopropyl)piperazine | 1,4-bis[3-(2-indanylcarbamylguanidino)propyl]piperazine dihydrochloride |
| 1-cyclohexylmethyl-4-methyl-4-isothiobiuret hydrochloride | N,N-bis(3-aminopropyl)-methylamine | 1,7-bis(cyclohexylmethylcarbamylguanidino)-3-methyl-4-azaheptane trihydrochloride |
| 1-cyclohexylmethyl-4-methyl-4-isothiobiuret hydrochloride | 1,4-bis(2-aminoethyl)piperazine | 1,4-bis[2-(cyclohexylmethylcarbamylguanidino)ethyl]piperazine dihydrochloride |
| 1-cyclohexylmethyl-4-methyl-4-isothiobiuret hydrochloride | 1,4-bis(3-aminopropyl)-1,4-diazacycloheptane | 1,4-bis[3-(cyclohexylmethylcarbamylguanidino)propyl]-1,4-diazacycloheptane dihydrochloride |
| 1-cyclohexylmethyl-4-methyl-4-iso-2,4-dithiobiuret hydrochloride | N,N-bis(2-aminoethyl)methylamine | 1,5-bis(cyclohexylmethylthiocarbamylguanidino)-3-methyl-3-azapentane trihydrochloride |
| 1-cyclohexylmethyl-4-methyl-4-isothiobiuret methanesulfonic acid salt | 1,4-bis(2-aminoethyl)piperazine | 1,4-bis[2-(cyclohexylmethylcarbamylguanidino)ethyl]piperazine dimethanesulfonic acid salt |
| 1-cyclohexylmethyl-4-methyl-4-isothiobiuret hydrochloride | bis(3-aminopropyl)methylamine | 1,7-bis[(cyclohexylmethyl)carbamylguanidino]-4-methyl-4-azaheptane dihydrochloride |
| 1-cyclohexylmethyl-4-methyl-4-isothiobiuret hydrochloride | 5,8-dimethyl-2,5,8,11-tetraazadodecane | 1,10-bis[(cyclohexylmethyl)carbamylamidino]-1,4,7,10-tetramethyl-1,4,7,10-tetraazadecane dihydrochloride |
| 1-(1-adamantyl)-4-methyl-4-isothiobiuret methanesulfonic acid salt | 1,4-bis(2-aminoethyl)piperazine | 1,4-bis[2-((1-adamantyl)carbamylguanidino)ethyl]piperazine dimethanesulfonic acid salt |
| 1-(1-adamantyl)-4-methyl-4-isothiobiuret methanesulfonic acid salt | 1,4-bis(4-aminobutyl)piperazine | 1,4-bis[4-((1-adamantyl)carbamylguanidino)butyl]piperazine dimethanesulfonic acid salt |
| 1-(1-adamantyl)-4-methyl-4-isothiobiuret methanesulfonic acid salt | 1,4-bis(2-aminopropyl)piperazine | 1,4-bis[2-((1-adamantyl)carbamylguanidino)propyl]piperazine dimethanesulfonic acid salt |
| 1-t-butyl-4-methyl-4-isothiobiuret methanesulfonic acid salt | 1,4-bis(3-aminopropyl)piperazine | 1,4-bis[3-(t-butylcarbamylguanidino)propyl]piperazine dimethanesulfonic acid salt |
| 1-cycloheptyl-4-methyl-4-isothiobiuret methanesulfonic acid salt | 1,4-bis(3-aminopropyl)piperazine | 1,4-bis[3-(cycloheptylcarbamylguanidino)propyl]piperazine dimethanesulfonic acid salt |
| 1-n-hexyl-4-methyl-4-isothiobiuret methanesulfonic acid salt | 1,4-bis(3-aminopropyl)piperazine | 1,4-bis[3-(n-hexylcarbamylguanidino)propyl]piperazine dimethanesulfonic acid salt |
| 1-(1-cyclohexylethyl)-4-methyl-4-isothiobiuret methanesulfonic acid salt | 1,4-bis(2-aminoethyl)piperazine | 1,4-bis[2-((1-cyclohexylethyl)carbamylguanidino)ethyl]piperazine dimethanesulfonic acid salt |
| 1-tert-octyl-4-methyl-4-isothiobiuret methanesulfonic acid salt | 1,4-bis(2-aminoethyl)piperazine | 1,4-bis[2-(tert-octylcarbamylguanidino)ethyl]piperazine dimethanesulfonic acid salt |

EXAMPLE VI 1-(Hexyl)-4-methyl-4-isothiobiuret hydrochloride, 1-(1-methylhexyl)-4-methyl-4-isothiobiuret hydrochloride, 1-(1,1,3,3-tetramethylbutyl)-4-methyl-4-isothiobiuret hydrochloride and 1-(1-adamantyl)-4-methyl-4-isothiobiuret methanesulfonic acid salt were each reacted with bis(3-aminopropyl)-methylamine according to the procedure described in Example IV to give, respectively, the following products:

1,7-bis(hexylcarbamylguanidino)-4-methyl-4-azaheptane as the dihydrochloride containing some trihydrochloride and melting at about 60°–70° C.

1,7-bis[(1-methylhexyl)carbamylguanidino]-4-methyl-4-azaheptane as the dihydrochloride containing some trihydrochloride and melting at about 60°–80° C.

1,7-bis[(1,1,3,3-tetramethylbutyl)carbamylguanidino]-4-methyl-4-azaheptane as the dihydrochloride melting at about 106°–110° C. with decomposition.

1,7-bis[(1-adamantyl)carbamylguanidino]-4-methyl-4-azaheptane as the salt with two moles of methanesulfonic acid and melting at about 162°–164° C.

The above compounds were tested for their activity against the microorganism *S. Mutans,* Strain OMZ-176E, in the serial dilution procedure described earlier and all were found to be active.

EXAMPLE VII

This example shows the antimicrobial effectiveness of the compounds of this invention in vitro.

The minimum inhibitory concentration of a number of compounds of this invention with respect to the microorganism *S. Mutans,* Strain OMZ-176E were determined by the procedure described above. The results are tabulated in Table III. Chlorohexidine diacetate, a commercially successful antimicrobial, was used as a control.

TABLE III

| COMPOUND | MIC γ/ml |
| --- | --- |
| 1,7-bis(4-chlorophenylcarbamylguanidine)-4-methyl-4-azaheptane | 0.625 |
| 1,4-bis[3-(4-chlorophenylcarbamylguanidino)propyl]piperazine | 0.156–0.312 |
| 1,8-bis(4-chlorophenylcarbamylguanidino)-3,6-dimethyl-3,6-diazaoctane | 1.25 |
| 1,4-bis[3-(1-adamantylcarbamylguanidino)propyl]piperazine dihydrochloride | 0.625 |
| 1,4-bis[(3-cyclohexylmethylcarbamylguanidino)propyl]piperazine dihydrochloride | 1.25 |
| 1,4-bis[3-(1,1,3,3-tetramethylbutylcarbamylguanidino)propyl]piperazine dihydrochloride | 1.25 |
| 1,4-bis[3-(n-octylcarbamylguanidino)proply]piperazine dihydrochloride | 2.50 |
| 1,4-bis[3-(2-ethylhexylcarbamylguanidino)propyl]piperazine dihydrochloride | 5.0 |
| 1,4-bis[3-(2-(4-chlorophenyl)ethylcarbamylguanidino)propyl]piperazine dihydrochloride | 1.25 |
| chlorhexidine diacetate. | 0.156–0.312 |

EXAMPLE VIII

A number of compounds of this invention were tested for in vitro antimicrobial activity against several pathogenic microorganisms using the above-described procedure except that trypticase soy broth was used in place of half strength brain-heart infusion as the medium. The results, which are given in Table IV, show that the compounds of this invention have antimicrobial activity against the common pathogens *E. coli, S. aureus, C. albicans, A. niger,* and *Ps. aeruginosa.*

TABLE IV

| Compound | MINIMUM INHIBITORY CONCN. MCG/ML | | | | |
| --- | --- | --- | --- | --- | --- |
| | E. coli | S. aureus | Ps. aeruginosa | C. albicans | A. niger |
| 1,4-bis[3-(cyclohexylmethylcarbamyl-guanidino)propyl]piperazine dimethanesulfonic acid salt | 6.25 | 0.78 | 100 | 6.25 | 12.5 |
| 1,4-bis[3-((1-adamantyl)carbamyl-guanidino)propyl]piperazine dimethanesulfonic acid salt | 25. | 6.25 | 50 | 12.5 | 12.5 |
| 1,4-bis[3-(cyclohexylcarbamylguanidino)propyl]piperazine dimethanesulfonic acid salt | 100. | 50. | 100 | 50. | 100. |
| 1,4-bis[3-(cycloheptylmethyl-carbamylguanidino)propyl]piperazine dimethanesulfonic acid salt | 12.5 | 0.78 | 12.5 | 0.78 | 50. |
| 1,4-bis[2-((1-adamantyl)carbamyl-guanidino)ethyl]piperazine dimethanesulfonic acid salt | 12.5 | 0.39 | 6.25 | 0.78 | 50. |
| 1,4-bis[3-((1-methylhexyl)carbamyl-guanidino)propyl]piperazine dihydrochloride | 12.5 | 1.56 | 25 | 6.25 | 25. |
| Chlorhexidine diacetate | 1.56 | 0.39 | 50 | 3.12 | 12.5 |

EXAMPLE IX

The staining properties of the compound of Example II were compared with those of chlorhexidine by the following procedure.

Test solutions were prepared containing 0.2% and 1% of chlorhexidine and 0.2% and 1% of the compound of Example II as the trimethanesulfonate salt.

Extracted human incisors, which were used without cleaning or other treatment which would remove the dental pellicle, were suspended from wires. Daily, each tooth was immersed for 10 minutes, in one of the test solutions, then suspended in whole stimulated saliva and incubated at 37° C. for 24 hours.

After ten days of exposure of the teeth to the test solutions, a greyish-brown discoloration was noted only on the teeth exposed to chlorhexidine. The amount of discoloration appeared to be independent of the concen-

What is claimed is:

1. A compound having the formula Z—B—Y—B—Z wherein Y is a nitrogen-containing alkylene group having the structural formula:

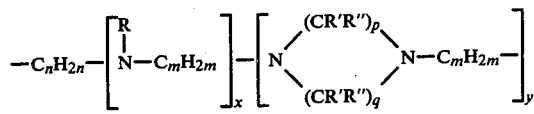

wherein
$n = 2-4$
$m = 2-4$
$p = 2,3$
$q = 2-4$
$x = 0-3$
$y = 0-2$
and $x=0$ when $y \neq 0$ and $y=0$ when $x \neq 0$, and R is hydrogen or $C_1-C_8$ hydrocarbon radical selected from the group consisting of alkyl, alkenyl, alkynyl, cycloalkyl, and aralkyl radicals; R' and R'' are each hydrogen or $C_1-C_4$ alkyl and may be the same or different; B is a substituted guanidino group selected from the group consisting of carbamylguanidino and thiocarbamylguanidino, with the proviso that when p and q are both equal to 2, then B is not a carbamylguanidino in which the guanidino portion is attached to Y; and Z is selected from the group consisting of $C_1-C_{12}$ alkyl; di($C_1-C_{10}$)alkylamino-$C_{10}-C_2$ alkyl having a total carbon content of $C_4-C_{12}$; $C_3-C_{12}$ alkenyl; $C_3-C_{12}$ alkynyl, $C_3-C_{12}$ cycloalkyl, $C_4-C_{12}$ cycloalkylalkyl, $C_6-C_{12}$ cycloalkenyl, $C_7-C_{14}$ cycloalkenylalkyl, $C_8-C_{12}$ polycycloalkyl, $C_9-C_{14}$ polycycloalkylalkyl, $C_8-C_{12}$ polycycloalkenyl, $C_9-C_{14}$ polycycloalkenylalkyl, $C_1-C_{10}$-alkoxy-$C_{10}-C_2$ alkyl having a total carbon content of $C_3-C_{14}$; $C_1-C_{10}$ alkylthio-$C_{10}-C_2$ alkyl having a total carbon content of $C_3-C_{14}$; phenoxy $C_2-C_6$ alkyl; phenylthio $C_2-C_6$ alkyl; $C_6-C_{14}$ aryl; $C_7-C_{14}$ aralkyl and arylcycloalkyl; $C_9-C_{12}$ benzocycloalkyl, and $C_6-C_{14}$ aryl and aralkyl substituted with one or more radicals selected from the group consisting of lower alkyl, trifluoromethyl, loweralkoxy, trifluoromethoxy, phenoxy, loweralkylthio, halo, nitro, cyano, $C_2-C_6$ alkanoyl, benzoyl, loweralkoxycarbonyl, diloweralkylamino, loweralkylsulfonyl, fluorosulfonyl and loweralkylsulfinyl; and pharmacologically acceptable addition salts of these compound with acids.

2. A compound according to claim 1 having the formula:

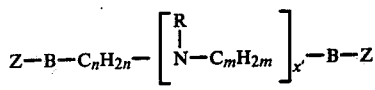

wherein B, R, Z, m and n are defined as above and x' is 1-3.

3. A compound according to claim 2 having the formula:

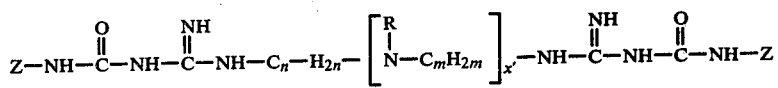

wherein R, Z, m and n and x' are defined as above.

4. A compound according to claim 3 wherein Z is selected from the group consisting of $C_4-C_{12}$ alkyl, $C_5-C_{10}$ cycloalkyl, $C_6-C_{10}$ cycloalkylalkyl, $C_6-C_{10}$ cycloalkenylalkyl, phenyl, naphthyl, phenyl $C_1-C_4$ alkyl, phenyl $C_3$ cycloalkyl, $C_1-C_4$ alkylphenyl, $C_1-C_3$ alkylbenzyl, trifluoromethylphenyl, trifluoromethylbenzyl, trifluoromethylphenylethyl, $C_1-C_4$ alkoxyphenyl, trifluoromethoxyphenyl, phenoxyphenyl, $C_1-C_4$ alkylthiophenyl, halophenyl, halobenzyl, halophenylethyl, $C_2-C_4$ alkanoylphenyl, $C_1-C_4$ alkoxycarbonylphenyl, $C_1-C_4$ alkylsulfonylphenyl and trifluoromethylphenylethyl.

5. A compound according to claim 3 wherein Z is selected from the group consisting of 2-ethylhexyl, 1,5-dimethylhexyl, 1,3-dimethylpentyl, 1,4-dimethylpentyl, 1,1,3,3-tetramethylbutyl, 1-methylhexyl, cyclohexylmethyl, cycloheptylmethyl, cyclopentylmethyl, 3-cyclohexen-1-ylmethyl, phenyl, 4-tolyl, 1-phenylethyl, 3-trifluoromethylphenyl, 4-trifluoromethylphenyl, 4-ethoxyphenyl, 3-methylthiophenyl, 4-methylthiophenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 4-methylthio-3-chlorophenyl, 1-adamantyl, 2-norbornyl, 1-adamantylmethyl, 1-(4-chlorophenyl)-ethyl, 2-(4-chlorophenyl)ethyl, and 2-(3-trifluoromethylphenyl)-ethyl.

6. A compound according to claim 3 having the formula:

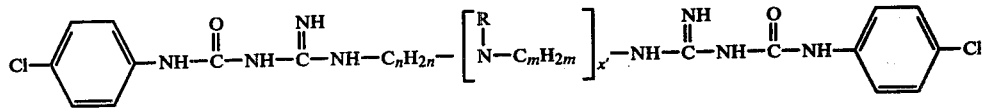

wherein R, m, n and x' are defined as above.

7. A compound according to claim 3 having the formula:

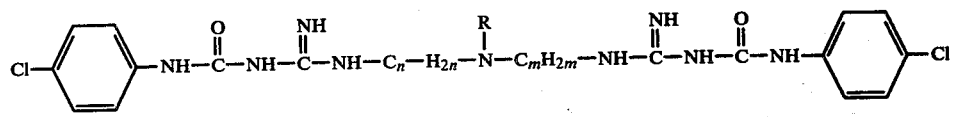

wherein R, m and n are defined as above.

8. A compound according to claim 2 which is 1,7-bis-(4-chlorophenylcarbamylamidino)-1,4-dimethyl-1,4,7-triazaheptane.

9. A compound according to claim 3 which is 1,7-bis-(4-chlorophenylcarbamylguanidino)-4-methyl-4-azaheptane.

10. A compound according to claim 3 which is 1,8-bis-(4-chlorophenylcarbamylguanidino)-3,6-dimethyl-3,6-diazaoctane.

11. A compound according to claim 3 having the formula:

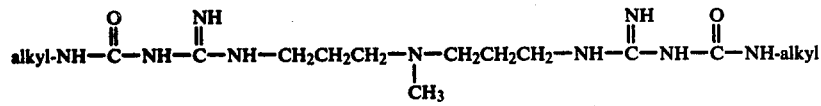

wherein alkyl is defined as above.

12. A compound according to claim 3 which is 1,7-bis-(hexylcarbamylguanidino)-4-methyl-4-azaheptane and pharmacologically acceptable acid addition salts thereof.

13. A compound according to claim 3 which is 1,7-bis-[(1-methylhexyl)carbamylguanidino]-4-methyl-4-azaheptane and pharmacologically acceptable acid addition salts thereof.

14. A compound according to claim 3 which is 1,7-bis-[(1,1,3,3-tetramethylbutyl)carbamylguanidino]-4-methyl-4-azaheptane and pharmacologically acceptable acid addition salts thereof.

15. A compound according to claim 3 which is 1,7-bis-[(1-adamantyl)carbamylguanidino]-4-methyl-4-azaheptane and pharmacologically acceptable acid addition salts thereof.

* * * * *

UNITED STATES PATENT AND TRADEMARK OFFICE
CERTIFICATE OF CORRECTION

PATENT NO. : 4,166,827

DATED : September 4, 1979

INVENTOR(S) : Julius Diamond

It is certified that error appears in the above-identified patent and that said Letters Patent are hereby corrected as shown below:

Column 2, lines 31 and 32, "*alkynyl*" should read --alkynyl--.
Column 3, line 24, "(1971)" should read (1971))--. Column 5, line 17, "cis-hexahydroidan" should read --cis-hexahydroindan--.
Column 7, line 4, "dimethylpentyl." should read --dimethylpentyl,--. Column 8, line 32, "salicyclic acid" should read --salicylic acid--. Column 9, line 6, "isocycnate" should read --isocyanate--. Column 9, line 30, "diisocycnate" should read --diisocyanate--. Column 15, line 36, "NH" on the right hand side of the formula should read --$NH_2$--.
Column 18, line 33, "249 263" should read --249-263--.
Column 20, line 8, "(7.65) g," should read --(7.65 g,--.
Column 22, Table I, 2nd Product name, "guanidino-" should read --guanidino)- --. Column 22, Table I, Product 6, "[3-trifluoro" should read --[3-(3-trifluoro--. Column 22, Table II, 2nd Product from bottom "1,4-bis 3" should read --1,4-bis[3--. Column 24, Table II, Product 10, "[3-(1-4" should read --[3-(1-(4--. Column 24, Table II, Product 12, "benzyl,carbamyl-" should read --benzylcarbamyl- --.
Column 24, Product 13, "ylmethyl)carbamyl-" should read -- ylmethylcarbamyl- --. Columns 23 and 24, Diamine 21 and

UNITED STATES PATENT AND TRADEMARK OFFICE
CERTIFICATE OF CORRECTION

PATENT NO. : 4,166,827

DATED : September 4, 1979

INVENTOR(S) : Julius Diamond

It is certified that error appears in the above—identified patent and that said Letters Patent are hereby corrected as shown below:

Product 21, the Diamine column should read "N,N-bis(3-aminopropyl)methylamine" and the Product column should read "1,7-bis-cyclohexylmethylcarbamylguanidino)-4-methyl-4-azaheptane trihydrochloride". Column 23, Isothiobiuret 34, "-4-methyl-isothio-" should read -- -4-methyl-4-isothio- --. Column 26, Table III, Compound 7,"proply" should read --propyl--.

Signed and Sealed this

Nineteenth Day of February 1980

[SEAL]

Attest:

SIDNEY A. DIAMOND

Attesting Officer     Commissioner of Patents and Trademarks